United States Patent [19]
Whynall et al.

[11] Patent Number: 6,053,030
[45] Date of Patent: Apr. 25, 2000

[54] INSTRUMENT INFORMATION AND IDENTIFICATION SYSTEM AND METHOD

[75] Inventors: Jeffrey M. Whynall, Killingworth; Rui Costa, Rocky Hill; Stanley Michnowicz, East Hampton; Christopher Boone, Branford; Michael Pawlyk, Ansonia, all of Conn.

[73] Assignee: Bacou USA Safety, Incorporated, Smithfield, R.I.

[21] Appl. No.: 09/235,973

[22] Filed: Jan. 22, 1999

[51] Int. Cl.[7] .............................. G06F 15/46; F04B 15/08; G01B 21/00; G08B 23/00
[52] U.S. Cl. ............................. 73/23.2; 73/31.02; 73/40; 340/825.49; 340/632; 364/188; 364/478.03
[58] Field of Search ........................... 73/23.2, 40, 31.02; 364/188, 478.14, 478.1, 478.03; 340/605, 632, 825.15, 825.49

[56] References Cited

U.S. PATENT DOCUMENTS

| | | |
|---|---|---|
| 4,570,217 | 2/1986 | Allen et al. .............................. 364/188 |
| 4,835,521 | 5/1989 | Andrejasich et al. ................... 340/521 |
| 4,869,874 | 9/1989 | Falat ........................................... 422/53 |
| 4,900,252 | 2/1990 | Liefke et al. .............................. 433/27 |
| 5,289,372 | 2/1994 | Guthrie et al. ........................... 364/403 |
| 5,469,369 | 11/1995 | Rose-Pehrsson et al. .............. 364/497 |
| 5,586,050 | 12/1996 | Makel et al. ............................. 364/509 |
| 5,632,957 | 5/1997 | Heller et al. ............................ 422/68.1 |
| 5,905,436 | 5/1999 | Dwight et al. ........................ 340/573.1 |

*Primary Examiner*—Hezron Williams
*Assistant Examiner*—J. David Wiggins
*Attorney, Agent, or Firm*—Cantor Colburn LLP

[57] ABSTRACT

The present invention is an instrument identification system and method for a confined space gas detector used to assure user safety conditions or to collect gas concentration and gas type data at a multitude of known predetermined locations. The system consists of information buttons with touch sensor contacts used for transferring ID type data comprising small stainless steel canisters containing computer memory programmed to store data pertaining to individuals and locations. The system further comprises a receptacle connector with electrical contacts coupled to a confined space gas detector for transferring information from the information buttons, where the gas detector, receptacle and receptacle contacts are contained within a portable integral housing.

15 Claims, 3 Drawing Sheets

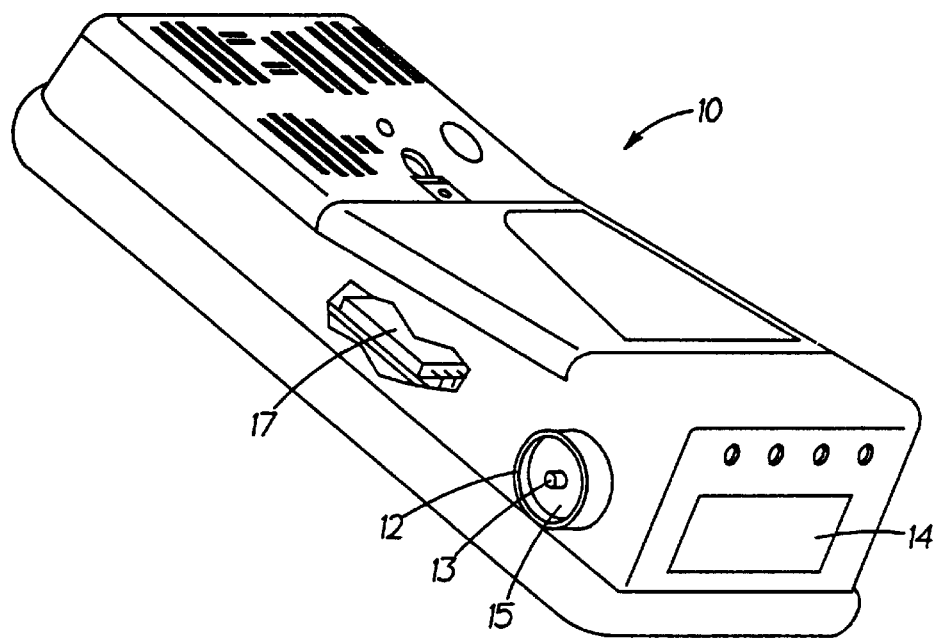
FIG. 1
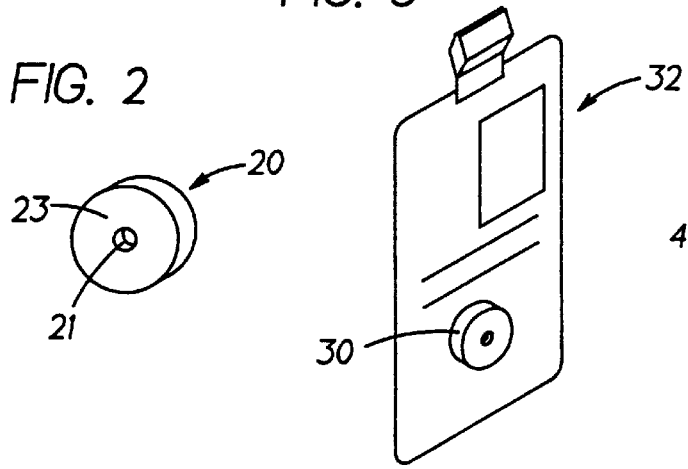
FIG. 2
FIG. 3
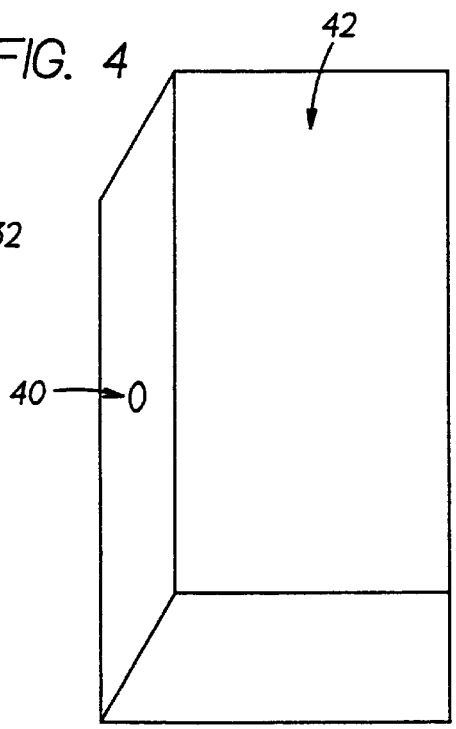
FIG. 4

INSTRUMENT INFORMATION AND IDENTIFICATION SYSTEM AND METHOD

BACKGROUND OF THE INVENTION

1. Field of the Invention

This invention relates generally to identification systems, and especially relates to an identification system and method for gas detection instruments.

2. Brief Description of the Related Art

Gas detection instruments are utilized in industry to detect the presence and quantities of gases in a particular environment. In a certain segment of industry gas detection instruments are used to determined the presence and concentrations of harmful gases to which workers may be exposed while performing a variety of duties. Such duties include maintenance of equipment and facilities, inspections, calibrations, and other similar tasks. It is common that individuals perform these tasks in confined, or closed, spaces that may contain harmful gases. The gases may be given off as by-product of a controlled process or known source or may enter the closed space by way of a leak from an unknown source. In any event, it is common to protect workers from prolonged exposure to harmful gases by using a gas detection instrument which monitors for the presence of gases, concentrations of gases and time exposure to the gases.

Typically a gas detection instrument and information transfer system is used by individuals performing tasks where gases may be present. The information transferred to the instrument documents what individual uses the instrument (User ID) and where the instrument is used (Location ID). The information is only useful for prior art gas detection instruments that record gas exposures to non-volatile memory. A real time clock is typically incorporated into the design of data-logging models that provides a time-stamp for each recorded data point. Each time the instrument is turned on a new "session" is started and the User ID and Location ID are committed to memory along with the measured gas levels. The interval at which records are made is typically one minute but may vary from one second to one hour.

An important use of such detection systems is the ability to track and maintain long-term exposure records of certain gases for individual employees. These records are helpful in documenting compliance with worker-safety regulations as well as supportive evidence for workman's compensation claims. Another important use of such detection systems is recording and maintaining records for each location (manholes, sewers, process vessels, electrical vaults, phone equipment vaults, etc.) so that gas levels may be observed and if abnormal levels of gases are detected on a regular basis in a particular location, remedial action can be taken.

A typical gas detection instrument, such as a Ph5 or PhD Lite manufactured by Biosystems Division of BACOU USA Safety Inc., is issued to an individual prior to entering a closed space which may contain a harmful gas. The gas detection instrument includes a data entry device wherein the individual, or user, inputs information specifying the user and further inputs information identifying the location where the detection instrument is to be used for a particular work session. An example of a prior art detection instrument includes a key pad wherein the user selects a user ID string and a location ID string from a list of such ID's stored in the memory of the instrument. In one such example an individual uses two of the keys to scroll down a list of alphanumeric choices and uses a third key to make a selection. In another prior art example a portable PC is used to input user and location information into the detection instrument. In such an embodiment, the PC is electrically connected to the instrument and a user selects a user ID string and a location ID string from a list of such ID's stored in memory on the PC and downloads the pertinent information in to the instrument.

One problem with the prior art detection instrument systems is that it is extremely easy for a user to input incorrect information. A user is required to navigate several menus and remember specific key stroke sequences to enter and/or activate the identification strings. As a result a user may incorrectly select the wrong user or location identification strings from the lists without knowing or having a way to verify or change the selection. Another problem with the prior art concerns the inability to easily add or change user or location identification strings. If the user or location is not preprogrammed into the instrument issued to a user the purpose of the detection instrument is obviated. In addition, the amount of information that may be transferred by prior art systems is extremely limited. An additional problem with the prior art concerns the systems that use a PC for downloading information to the instrument. In using such instruments, it becomes burdensome to transport and safely store the PC while a user performs the underlying tasks suggested herein above. In addition, the use of a PC requires increased skill levels of an operator and increases the cost of the detection instrument system.

In another detection instrument system of the prior art, a conventional bar code and wand is used to input user and location identification strings. In such systems, a bar code reader is connected to a detection instrument which is used to scan bar code labels pertaining to users and locations. Although bar code instruments eliminate some the problems present in other prior art detection systems, they too have many problems. One problem, similar to the PC systems, is that a bar code reader must be attached to and therefore transported along with, the detector. Another problem is that the bar code labels typically do not withstand some of the harsh environments in which these instruments are typically used. Reprogramming of bar coded labels is also difficult. Other problems, also common with PC linked detectors, the attachment of peripheral devices to the detector comprises the environmental integrity of the detector from a moisture ingression and radio-frequency interference susceptibility standpoint. This also creates an explosion hazard.

What is needed in the art is a reliable gas detection instrument identification system which increases accuracy, system flexibility, ease of use and one that functions well in harsh environments.

SUMMARY OF THE INVENTION

The above-described drawbacks and disadvantages of the prior art are alleviated by the gas detection instrument identification system of the present invention. The gas detection instrument identification system comprises at least one User ID touch sensor, on e Location ID touch sensor, and a gas detection instrument including a Touch ID receptacle connector.

The above discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES:

FIG. 1 is an isometric view of a gas detection instrument showing the receptacle connector in accordance with the present invention;

FIG. 2 is an isometric view of an information button;

FIG. 3 is an isometric view of an identification badge showing a User ID in accordance with the present invention;

FIG. 4 is an isometric view of an entrance to a confined space showing a Location ID in accordance with the present invention;

Figure 5:
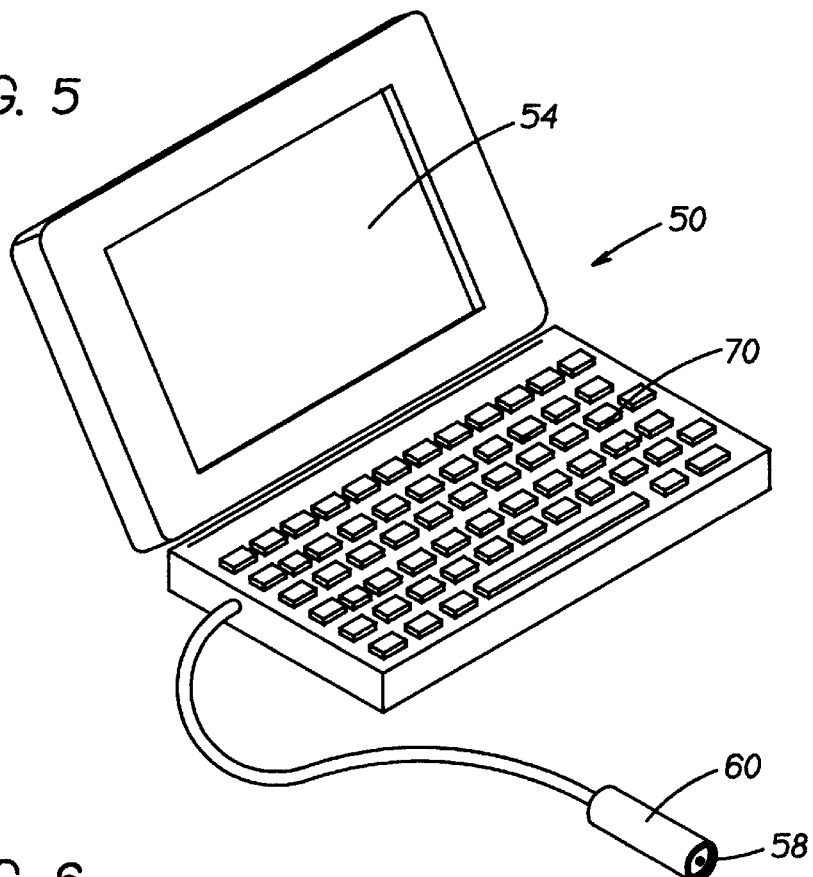
FIG. 5 is an isometric view of a personal computer showing a wand in accordance with the present invention.

The figures are meant to further illustrate the present invention and not to limit the scope thereof.

DETAILED DESCRIPTION OF THE PREFERRED EMBODIMENT

A confined space gas detection instrument in accordance with the present invention is shown generally as 10 in FIG. 1. Detector 10 is similar to that described herein above and is used to monitor gases in confined spaces including oxygen, combustible gas, carbon monoxide, and hydrogen sulfide. In accordance with the present invention detector 10 includes receptacle connector 12 mounted to a side of the detector. Receptacle connector 12, also referred to as a receptor, is electrically connected to a data port of detector 10 and is used to transfer information to the detector. In an alternative embodiment (not shown) receptacle connector 12 is integrally molded into the side of detector 10 to eliminate external attachments to the detector and the environmental and interference problems described herein above. Receptacle connector 12 further comprises two contacts 13, 15. Referring to FIG. 2 there is shown an information button 20 comprising a computer chip preferably encased within a stainless steel housing and containing computer memory on which to store information. Information button 20 resembles a watch battery, as is known, and comprises two separate contacts 21, 23 to mate with contacts 13, 15. In an embodiment of the present invention receptacle connector 12 is a Blue Dot Receptor and information button 20 is an iButton™, both manufactured by Dallas Semiconductor.

Information button 20 is comprised of a silicon chip having a unique registration number engraved therein. The button further includes a computer memory medium storing text strings pertaining to an individual, referred to as User ID 30 (FIG. 3), or text strings pertaining to a location, referred to as Location ID 40 (FIG. 4). Information is transferred from button 20 to detector 10 by placing the button within connector 12. Momentary contact of button 20 with connector 12 transfers information from the button to the detector at a rate of up to 142K bits per second. Detector 10 includes a microprocessor 17 comprising a 16 bit micro controller with 512 kbytes of flash memory and 32K of boot ROM. Detector 10 further includes appropriate software to interpret and manipulate the information transferred to provide a variety of functions including presenting messages and prompts for display on screen 14.

An example of a User ID 30 information button is shown in FIG. 3 as part of a typical identification badge 32 worn by an individual. User ID 30 is programmed to store information pertaining to the individual issued the identification badge 32. Typical information stored on the memory of User ID 30 includes a user mode level, a user language code and the identification of the user. Prior to beginning a session, a user places User ID 30 against connector 12 and the information is transferred to detector 10 as described herein above. Software residing in detector 10 then records the user information and manipulates the detector in accordance with the information pertaining to the specified user.

The user mode concerns the operating level of detector 10 with respect to the amount and type of information displayed on display 14 as well as the skill level of the user. In an embodiment of the present invention there are three user modes of operation including text mode, basic mode and technician mode. Text mode is tailored for a user with relatively low skills or experience level. While operating in this mode display 14 indicates "OK" if all gas readings are below pre-set alarm levels. If gas levels ascend past alarm levels, the text readings change into numerical readings corresponding to gas levels. The battery level is shown on display 14 in this mode as well. In addition, no calibrations are allowed while the instrument is in "Text Mode". In the user mode designated as basic mode instead of displaying "OK", detector instrument 10 displays gas readings in engineering units on display 14. The battery level is also shown on display 14 in this mode. Calibrations are allowed if the unit is in "Basic Mode". The user mode designated technician mode is reserved for very skilled users such as Industrial Hygienists or Safety Directors. Both displays from "Basic Mode" are available as well as additional displays are shown on display 14 in technician mode that, for example, indicate peak readings experienced since the instrument was turned on, as well as several more technical information displays.

The user language code is particular to the user and directs detector 10 to display readings and other information on display 14 in a particular language. For example, a User ID 30 for a particular Spanish speaking user would be programmed to contain a language code designating Spanish. After transfer the detector software will direct all information displayed on display 14 to be in Spanish language allowing the user to readily and accurately interpret the display.

The portion of the memory of User ID 30 allocated to user identification, in accordance with the present invention, includes information unique to a specific individual. Examples of such information includes name, employee number, photographic image, health restrictions, age, sex, social security number as well as other such specific personal information.

Referring now to FIG. 4 there is shown an example of a Location ID 40 information button located at entrance 42 of a confined space as described herein above.

Location ID 40 is similar to User ID 30 in size, shape and appearance but is preprogrammed to contain information specific to the location at which it is permanently mounted. In FIG. 4 Location ID 40 is shown mounted directly to entrance 42 but may be mounted within a container or box (not shown) to protect the button from the environment. Information programmed onto the memory of Location ID 40 includes the physical location of the button, a list of required sensors to be present within detector 10, security protocols, and other similar information pertaining to the physical location of the button. It is within the scope of the present invention that Location ID 40 also include information that would prompt a light to backlight display 14 if the confined space is normally dark; include specific alarm levels for certain types of gases; and other detector operating characteristics. Location ID may also include a temperature sensor, a clock or other similar type of environmental indicating sensor.

Figure 6:
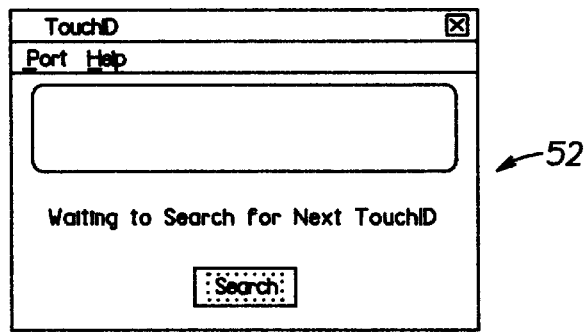
FIG. 6 is a graphical representation of a prompt screen of the present invention.
Figure 7:
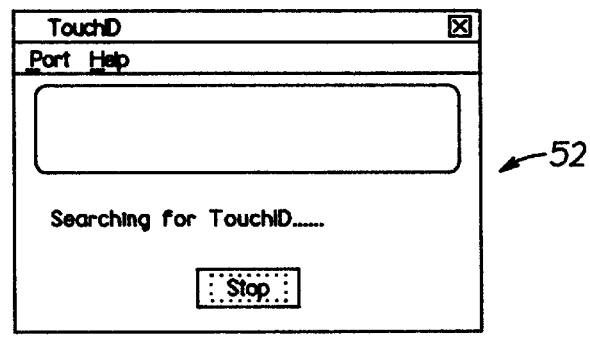
FIG. 7 is a graphical representation of another prompt screen of the present invention.
Figure 8:
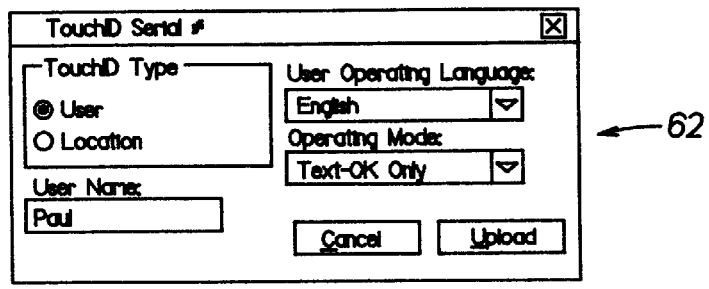
FIG. 8 is a graphical representation of yet another prompt screen of the present invention.
Figure 9:
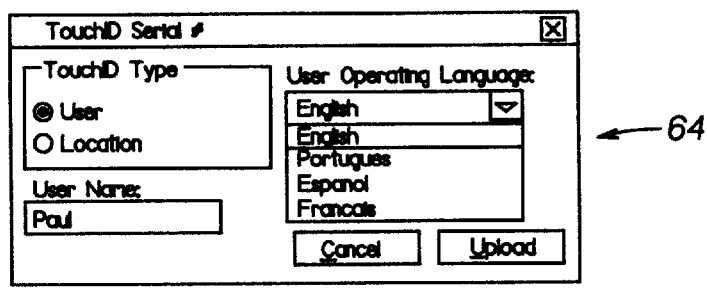
FIG. 9 is a graphical representation of yet another prompt screen of the present invention.
Figure 10:
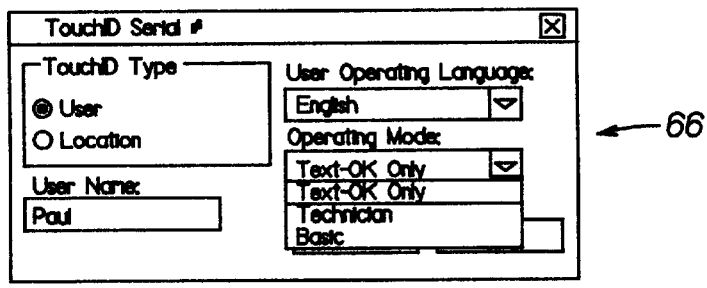
FIG. 10 is a graphical representation of yet another prompt screen of the present invention.
Figure 11:
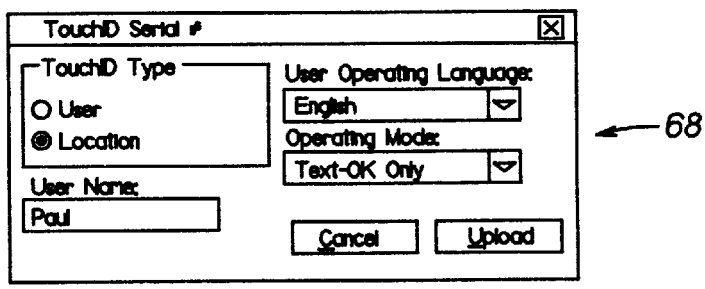
FIG. 11 is a graphical representation of still another prompt screen of the present invention.

In accordance with the present invention the information buttons 20, 30, 40 are preprogrammed to contain the above described information by an individual using the detector. In an alternative embodiment a separate computer using a programming kit comprising a wand 60 (FIG. 5) that connects to the serial port of PC 50 and programming software is used. Information can be added, changed, updated or deleted in a quick and efficient manner. With reference to FIGS. 5–11, in operation an individual launches Touch ID software resident on a PC 50 and waiting prompt 52 is displayed on screen 54 until "search" is selected by the individual. Prompt 56 is then displayed on screen 54 until the individual inserts a button 20 into receptacle 58 on wand 60.

Receptacle 58 is similar to receptacle 12 as described herein above and interfaces with electrical contacts 21, 23. Once button 20 is inserted into wand 60 the individual is led by prompts 62, 64, 66, 68 to program information, as shown and described herein above, into the button using keyboard 70. Once programming is complete the individual selects "upload" from the particular prompt and the information is transferred to the button 20.

In use an individual is issued an identification badge 32 including a User ID 30 (FIG. 3) that is unique and is preprogrammed to contain the above described user information specific to that individual. During the course of a work day the individual is assigned to work in a confined space wherein certain harmful gases may be present and is issued a confined space gas detection instrument 10 from a pool of instruments. The individual touches User ID 30 to connector 12 on detector 10 and the detector then begins a session including setting up the user mode, the language mode and the user information specific to the individual. The user then takes the detector to a confined work space, a pulp digester for example, where a Location ID is mounted at the entrance thereto. The individual touches the Location ID to the connector whereby location information is transferred to the detector. The individual enters the work space and while performing the assigned tasks detector 10 monitors the space for gases and records exposure time. Upon exiting the confined space the user again places the Location ID 40 against the connector whereby the exposure time is stopped and the data is stored within detector 10.

The individual may then proceed to a subsequent task within a confined space, such as a lime kiln for example, wherein a second Location ID is mounted and the sequence is repeated for that location. At the end of a specified work period the detector is returned to an Industrial Hygienist, or similar such person, wherein recorded information pertaining to the user, locations, exposure times and gases are downloaded and stored in a separate computer (not shown). The downloading operation is similar to other data transfer using the information buttons in that connector 12 is used to transfer the data to the separate computer. On a subsequent day the same detector may be issued to another individual performing different operations. The information transferred to and subsequently stored on the computer is accurate an timely because it is free of human entry errors as a result of using the instrument identification system comprising a User ID, a Location ID, and connectors and the methods outlined herein in accordance with the present invention.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An information and identification system for a gas detection instrument used to assure user safety or to collect gas concentration and gas type data at a multitude of know predetermined locations comprising:

a user identification touch sensor associated with the particular user having user information programmed therein;

a location identification touch sensor attached to the particular location having location information programmed therein; and a receptacle electrically connected to the gas detection instrument receiving the user identification touch sensor and the location identification touch sensor via touch sensor contacts and receptacle contacts and transferring the user information and the location information to the gas detection instrument, where said gas detention instrument is contained in a portable integral housing and both of said receptacle and said receptacle contacts are attached to or contained in said portable integral housing.

2. The information and identification system as set forth in claim 1 wherein the gas detection instrument further comprises:

a microprocessor having a data port; and a first contact and a second contact disposed within the receptacle electrically connected to the data port.

3. The information and identification system as set forth in claim 2 wherein the microprocessor comprises a micro controller having flash memory and read only memory.

4. The information and identification system as set forth in claim 1 wherein the user touch sensor and the location touch sensor comprise a silicon chip having programmable memory storing the user information and the location information.

5. The information and identification system as set forth in claim 4, wherein the user touch sensor and the location touch sensor include first and second contacts.

6. The information and identification system as set forth in claim 5 wherein the memory of the user touch sensor stores text strings pertaining to an individual.

7. The information and identification system as set forth in claim 5 wherein the memory of the location touch sensor stores text strings pertaining to a location.

8. The information and identification system as set forth in claim 6, wherein the text strings include a user identification, a user level mode, a user language code unique to the individual, or combinations thereof.

9. The information and identification system as set forth in claim 7 wherein the text strings include a physical location description, a list of required sensors, security protocols unique to the location, or combinations thereof.

10. The information and identification system as set forth in claim 9 wherein the location touch sensor is disposed at an entrance to a predetermined location.

11. The information and identification system as set forth in claim 1 wherein the instrument includes software interpreting and manipulating the information and further includes a screen displaying messages and prompts based on the information.

12. An information and identification system for a gas detection instrument, comprising:

a user identification touch sensor associated with a particular user having user information programmed therein;

a location identification touch sensor attached to a particular location having location information programmed therein, wherein the location touch sensor comprises a silicon chip having programmable memory storing the location information, and wherein the memory of a the user touch sensor, having first and second contacts, stores text strings including a user identification, a user level mode, and a user language code unique to the individual; and a receptacle, electrically connected to the gas detection instrument receiving the user identification touch sensor and the location identification touch sensor and transferring the user information and the location information to the gas detection instrument.

13. A method of providing information and identification for a gas detection instrument contained within a portable integral housing, the instrument ensuring user safety or determining gas concentration and gas type data, the method comprising:

recording identification and information pertaining to a user onto memory contained on a user touch sensor associated with the particular user;

recording identification and information pertaining to a location onto memory contained on a user touch sensor;

mounting the location touch sensor to an entrance to a location;

placing the user touch sensor in contact via electrical contacts with a receptacle mounted on the gas detection instrument and thereby transferring and recording identification and information pertaining to the user onto memory contained in the gas detection instrument;

starting a sampling session by placing the receptacle in contact via electrical contacts with the location touch sensor and thereby enabling the gas detection instrument to an activated mode; and transferring and recording identification and information pertaining to the location onto memory contained in the gas detection instrument; and ending a sampling session by placing the receptacle in contact with the location touch sensor.

14. The method of claim 13 further comprising:

detecting gases with the gas detection instrument while enabled to said activated mode; and recording levels of and types of gases detected onto the memory of the gas detection instrument.

15. The method of claim 13 further comprising downloading the recorded information from the gas detection instrument to a personal computer.

* * * * *